(12) United States Patent
Li et al.

(10) Patent No.: US 11,825,788 B2
(45) Date of Patent: *Nov. 28, 2023

(54) METHOD FOR PROMOTING ACCUMULATION OF SECONDARY METABOLITES IN CANNABIS

(71) Applicant: Fujian Sanan Sino-Science Photobiotech Co., Ltd., Quanzhou (CN)

(72) Inventors: Shaohua Li, Quanzhou (CN); Yang Li, Quanzhou (CN); Guojie Liu, Quanzhou (CN); Yiqun Chen, Quanzhou (CN); Desheng Su, Quanzhou (CN); Shengshuang Xie, Quanzhou (CN)

(73) Assignee: FUJIAN SANAN SINO-SCIENCE PHOTOBIOTECH CO., LTD., Quanzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/384,714

(22) Filed: Jul. 24, 2021

(65) Prior Publication Data
US 2021/0345554 A1 Nov. 11, 2021

Related U.S. Application Data

(63) Continuation-in-part of application No. PCT/CN2019/106427, filed on Sep. 18, 2019.

(51) Int. Cl.
| | | |
|---|---|---|
| *A01H 3/02* | (2006.01) | |
| *A01G 7/04* | (2006.01) | |
| *A01G 7/06* | (2006.01) | |
| *A01G 9/20* | (2006.01) | |
| *A01G 22/00* | (2018.01) | |
| *F21V 9/30* | (2018.01) | |
| *A01G 22/15* | (2018.01) | |
| *A01H 6/28* | (2018.05) | |
| *F21Y 115/10* | (2016.01) | |
| *F21Y 113/17* | (2016.01) | |

(52) U.S. Cl.
CPC .............. *A01G 7/045* (2013.01); *A01G 7/06* (2013.01); *A01G 9/20* (2013.01); *A01G 22/00* (2018.02); *A01G 22/15* (2018.02); *A01H 3/02* (2013.01); *A01H 6/28* (2018.05); *F21V 9/30* (2018.02); *F21Y 2113/17* (2016.08); *F21Y 2115/10* (2016.08)

(58) Field of Classification Search
CPC ...................................................... A01H 3/02
See application file for complete search history.

(56) References Cited

PUBLICATIONS

Magagnini et al. 2018. The effect of light spectrum on the Mornphology and cannabinoid conent of *Cannabis sativa* L. Med. *Cannabis Cannabinoids.* 1: 19-27. (Year: 2018).*
Williams. 2017. What is a LED chip and why does it matter? HomElectrical website. https://www.homelectrical.com/what-led-chip-why-does-it-matter.6.html. (Year: 2017).*
Hawley et al. 2018. Improving Cannabis Bud Quality and Yield with Subcanopy Lighting. HortScience 53(11): 1593-1599. (Year: 2018).*
Magagnini, G. et al. "The Effect of Light Spectrum on the Morphology and Cannabinoid Content of *Cannabis sativa* L.," Medical Cannabis Cannabinoids, 2018, vol. 1: 19-27.
Paul, G. M. et al., "Effect of Light Quality on Cannabinoid Content of *Cannabis sativa* L. (*Cannabaceae*)," Bot.Gaz., 1983, 144(1): 43-48.
Hawley, D., "The influence of spectral quality of light on plant secondary metabolism and photosynthetic acclimation to light quality," Ph.D. dissertation, The University of Guelph., 2018, 163.
Bilodeau, S.E. et al., "An Update on Plant Photobiology and Implications for Cannabis Production," Front. Plant Sci., 2019, 10: 296.
Hawley, D. et al., "Improving Cannabis Bud Quality and Yield with Subcanopy Lighting," Hortscience, 2018, 53 (11): 5193-1599.
Ajinkya Lalge et al., "The Effects of Red, Blue and White Light on the Growth and Development of *Cannabis sativa* L.," Mendel Net, 2017, 24: 646-651, Brno Czech Republic.
Kim Hyeon-Hye et al., "Green-light Supplementation for Enhanced Lettuce Growth under Red- and Blue-light-emitting Diodes," HortScience, 2004, 39(7): 1617-1622.
Tingting Zhang et al., "Green light signaling and adaptive response," Plant Signaling & Behavior, 2012, 7(1): 75-78.

* cited by examiner

*Primary Examiner* — Karen M Redden

(57) ABSTRACT

A method for promoting the accumulation of secondary metabolites of cannabis is disclosed. The method comprises the step of adding an irradiation of green-yellow light, which has a peak wavelength at 505-590 nm, into the indoor growing environment of cannabis to improve the level of cannabidiol (CBD), secondary metabolites in cannabis. While maintaining the light intensity and other growth conditions, the yield and/or level of CBD, secondary metabolites in cannabis, can be increased by up to 11.04%.

3 Claims, 2 Drawing Sheets

METHOD FOR PROMOTING ACCUMULATION OF SECONDARY METABOLITES IN CANNABIS

CROSS REFERENCE TO RELATED APPLICATIONS

This application is a continuation in part of PCT patent Application No. PCT/CN2019/106427, filed on Sep. 18, 2019, entitled "Light Regulation Method for Promoting Accumulation of Secondary Metabolites in Cannabis Plants", which claims priority of U.S. patent application Ser. No. 16/446,602, filed on Jun. 19, 2019, in the USPTO, the entire content of which are hereby incorporated by reference in their entireties.

TECHNICAL FIELD

The subject matter herein relates to a technical filed of medicinal plants, and in particularly relates to a method for promoting accumulation of secondary metabolites in cannabis plants.

BACKGROUND

Cannabis (*Cannabis sativa* L.) is an annual erect herb. The main active ingredient in cannabis plants is cannabinoids. Currently, over 70 kinds of natural cannabinoids are found, which are mainly used in some nervous system diseases, such as multiple sclerosis, motor neuropathy, chronic intractable pain, a drug-induced vomiting. Tetrahydrocannabinol (THC) and cannabidiol (CBD) are the main active ingredients. In the biosynthetic pathway of cannabinoids, CBD and THC are decarboxylated from cannabidiolic acid (CBDA) and tetrahydrocannabinolic acid (THCA), respectively. CBDA and THCA share a common precursor of cannabidiolic acid (CBGA). After being catalyzed by THCA synthetase and CBDA synthetase, THCA and CBDA are produced respectively. This indicates that THC and CBD are in different branches of the cannabinoid synthesis pathway and are catalyzed by different enzymes. Different environmental factors may have different regulatory effects on the catalytic process of different enzymes.

The level of CBD is a key medicinal quality indicator of industrial hemp mosaic. As a non-psychoactive compound, CBD has excellent tolerance and above-average safety, and is widely used in the field of medical research. CBD exerts analgesic and anti-inflammatory effects through dual inhibition of cyclooxygenase and lipoxygenase. It also has potential medical value in the treatment of schizophrenia, Alzheimer's disease and epilepsy. It also has a good intervention effect for drug-induced mental dependence such as morphine, cocaine, alcohol or the like. The broad prospects of medical applications make CBD a hot spot in the research and development of cannabinoid drugs. Therefore, the cultivation technology of medicinal cannabis plants with high levels of CBD has become a difficult point that needs to be solved urgently.

Indoor cultivation of cannabis can obtain plant raw materials with stable level and yield of medicinal ingredients in full years without being affected by seasons, because the indoor cultivation of cannabis has stable environmental factors including light, temperature, humidity, nutrition and the like required for growth. Light is one of the most relevant environmental factors influencing plant behavior. It is not only the basic energy source for photosynthesis, but also an important regulator of plant growth and development, which plays a significant role in plants' morphogenesis, reproductive development, and regulation of secondary metabolites. Cannabis is a light-loving and short-day plant, which is sensitive to light. It is an important technical means to improve the secondary metabolites for medicinal components by adjusting the light quality ratio of the light environment in the growth of cannabis. The way to adjust the light quality ratio of the light environment is feasible and simple for implementation. It will become an effective technology for producing medicinal cannabis with high levels of CBD and provide a reliable way to provide high-quality raw materials for producing cannabinoid.

At present, high-pressure sodium lamps (HPS), metal halide lamps (MH), and light-emitting diode lights (LED) are mainly used to provide a light environment for indoor cannabis cultivation. HPS and MH are limited by their spectral design, and the achievable spectral energy distribution is limited. LED lights have the characteristics of narrow half-height and flexible spectral design, which have been widely studied. It has become an important research goal of high-quality and high-efficiency cultivation and production of medical cannabis to explore the cultivation methods for promoting accumulation of CBD. However, in the LED light spectrum matching method that promotes accumulation of secondary metabolites in plants, it has not yet disclosed how to promote the indoor cultivation and growth of cannabis plants to achieve a better effect of promoting accumulation of level of CBD, secondary metabolites in cannabis.

SUMMARY

With respect to the background, one object of the present disclosure is to provide a method for promoting accumulation of CBD level in cannabis by regulating a growing environment of cannabis.

Specifically, the object of the present disclosure is achieved by the following embodiments.

A method for promoting accumulation of CBD, secondary metabolites in cannabis. The method is achieved by adding an irradiation of green-yellow light having a peak wavelength at 505-590 nm in an indoor growing environment of cannabis to increase the accumulation of level and yield of CBD in cannabis.

In some embodiments, the step of adding the irradiation of green-yellow light having a peak wavelength at 505-590 nm comprises a combined irradiation with other wavelength bands or independent irradiation.

In some embodiments, in the combined irradiation with other wavelength bands, a ratio of the photon number of the green-yellow light to the photon number of the entire light source does not exceed 50%.

In some embodiments, the light source used in the indoor growing environment of cannabis is a LED light source.

In some embodiments, the LED light source is composed of 10-18.4% blue light, 40-73.6% red light, and 8-50% green-yellow light.

In some embodiments, the blue light has a peak wavelength at 440-460 nm, the red light has a peak wavelength at 655-690 nm, and the green-yellow light has a peak wavelength at 505-590 nm.

In some embodiments, the peak wavelength of the green-yellow light, preferably, lies at 505-526 nm and 590 nm.

In some embodiments, the LED light source comprises 16-42% green-yellow light.

In some embodiments, a ratio of the photon number of the blue light to the photon number of the red light is 1:4.

In some embodiments, the LED light source is realized directly by a LED chip or by using the LED chip to excite a phosphor material.

In some embodiments, an initial light intensity is 80 µmol/m²s, a maximum light intensity is 1000 µmol/m²s, and a photoperiod is 10-16 h/d.

Compared with the prior art, the present disclosure has the following advantages.

The present disclosure provides a method for promoting accumulation of secondary metabolites in cannabis. By introducing the irradiation of green-yellow light, which has a peak wavelength at 505-590 nm, into the indoor growing environment of cannabis, and maintaining the light intensity and other growth conditions, the yield and/or level of CBD, the secondary metabolites in cannabis, can be effectively promoted by at least 11.04%.

DETAILED DESCRIPTION OF THE INVENTION

The present disclosure will be further described in detail below with reference to the drawings and specific embodiments, in order to better understand the objective, the technical solution and the advantage of the present disclosure. It should be understood that the specific embodiments described herein are merely illustrative and are not intended to limit the scope of the disclosure.

Figure 1:
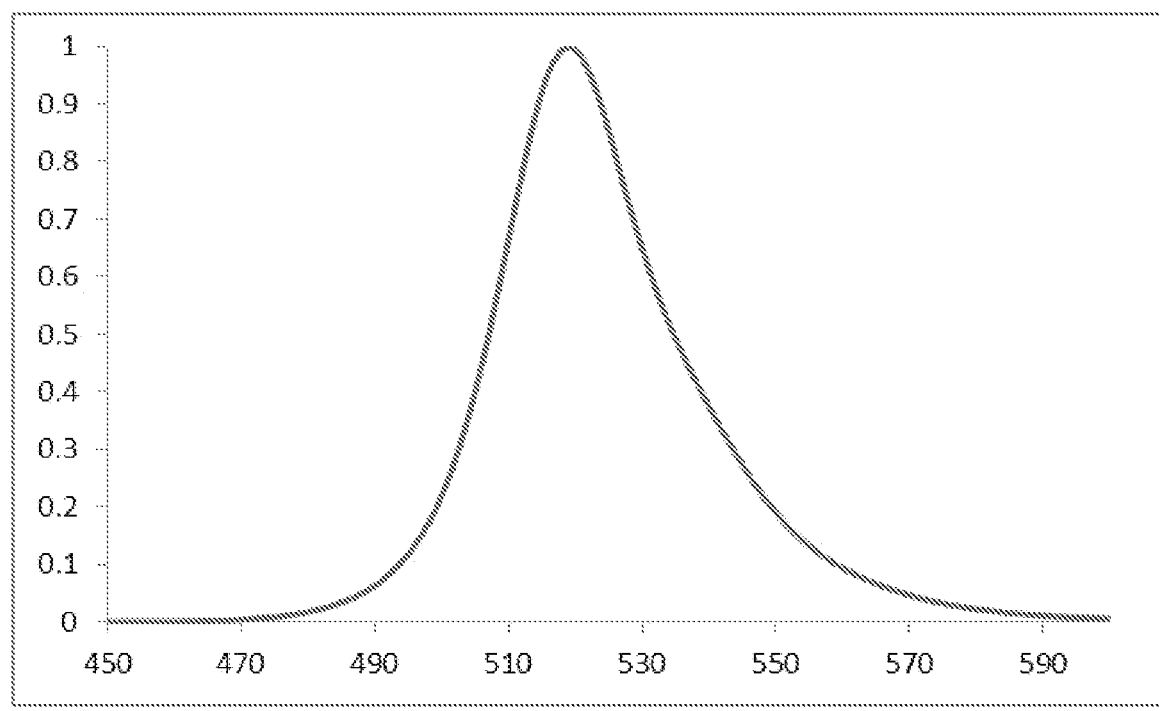
FIG. 1 is a spectral distribution diagram from a LED light source which is realized directly by a LED chip according to the present disclosure.
Figure 2:
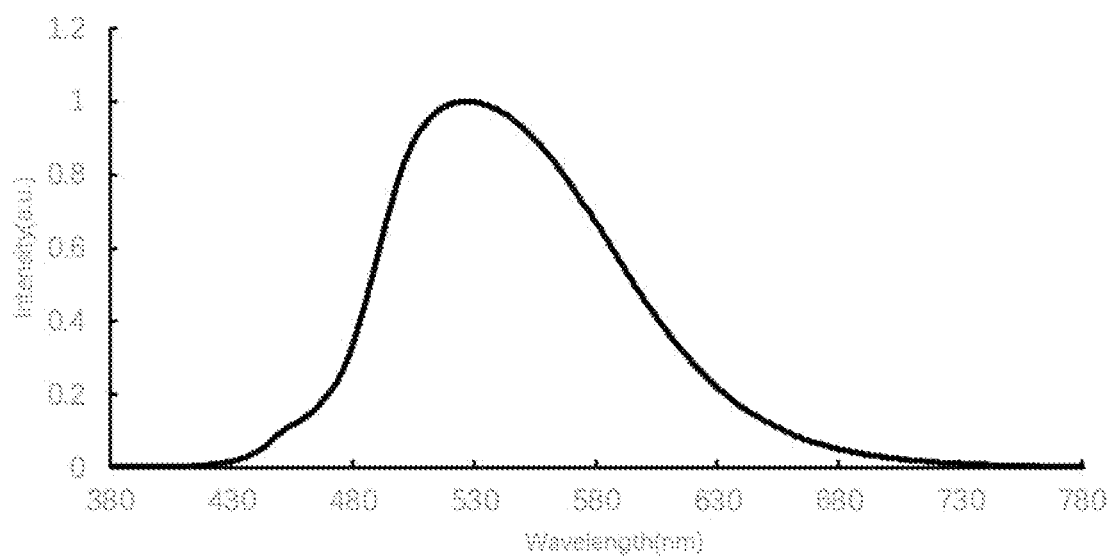
FIG. 2 is a spectral distribution diagram from a LED light source which is realized by using the LED chip to excite a phosphor material according to the present disclosure.
Figure 3:
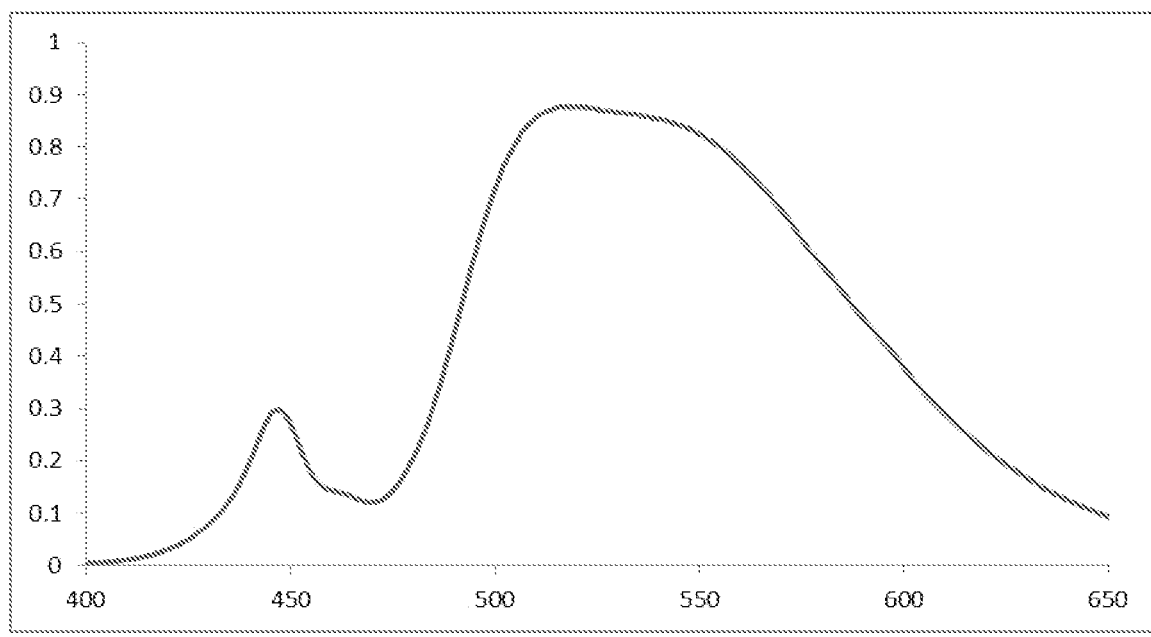
FIG. 3 is a spectral distribution diagram from a LED light source which is realized by using the LED chip to excite a phosphor material according to the present disclosure.

In the early stage of treatment to cannabis seedling, top branches of strong cannabis mother plant are selected as stem cuttings for plant cutting, or cannabis seeds are selected for sowing. The seedling stage is about 2 weeks. The cannabis seedlings with good rooting conditions are transplanted into the substrate or rock wool for the vegetative growth phase (the vegetative growth stage is about 4 weeks). Each rock wool block has 1 plant, and a density for the transplanted cannabis seedlings is 9 plants/m². The plant is topped when the plant is about 20 cm high for triggering the growth of side branches. After the vegetative growth stage is finished, the plant is moved to the flower promotion stage for flower promotion treatment. The planting density of the plant in the flower promotion stage is 4-6 plants/m². A distinguishment to the male and female flowers is required. The male flowers will be removed, and the female plants will be cultivated. The cultivation environment is set to have a day and night temperature at 24-26° C./21-22° C., humidity at 60-70%, $CO_2$ concentration at 10000 ppm. Throughout the growth process, the LED light source directly realized by the LED chip is an artificial light source. The spectrum distribution diagram directly realized by the LED chip is shown in FIG. 1. The LED light source as shown provides a light environment for the growth of cannabis. An initial light intensity is set to 80-100 µmol/m²s. As the plant height increases, the light intensity may reach 500-1000 µmol/m²s in the late stage, and the photoperiod is 10-16 h/d. After 7-9 weeks of growth at the flowering stage, the accumulation of levels of CBD, the secondary metabolites in the inflorescence of cannabis plants, would be promoted.

Embodiment 1

Top branches of strong cannabis mother plant are selected as stem cuttings for plant cutting. After the plant cutting is finished (the plant cutting stage is about 2 weeks), the cannabis seedlings with good rooting conditions are transplanted into the rock wool or the substrate for the vegetative growth phase (the vegetative growth stage is about 4 weeks). Each rock wool block has 1 plant, and a density for the transplanted cannabis seedlings is 9 plants/m². The plant is topped when the plant is about 20 cm high for triggering the growth of side branches. After the vegetative growth stage is finished, the plant is moved to the flower promotion stage for flower promotion treatment. The planting density of the plant in the flower promotion stage is 4 plants/m². A distinguishment to the male and female flowers is required. The male flowers are removed, and the female plants is cultivated as before. The cultivation environment is set to have a day and night temperature at 24-26° C./21-22° C., humidity at 60-70%, $CO_2$ concentration at 10000 ppm. Throughout the growth process, the LED light source is used to provide a light environment for the growth of the plant. An initial light intensity is set to 100 µmol/m²s. As the plant height increases, the light intensity reaches 550 µmol/m²s in the late stage, and the photoperiod is 12 h/d. A blue LED light source with a peak wavelength at 445 nm is provided as a control example, and green-yellow light sources with peak wavelengths at 505 nm, 515 nm, 526 nm, 571 nm are provided as 4 experimental examples. When harvesting, the CBD level in the cannabis is determined, and the dry weight of the inflorescence is collected at the same time to calculate the CBD yield of single plant. The experimental results are shown in Table 1.

TABLE 1

| Ind. Irradiation | Peak WL/nm | CBD level (%) | Inflorescence DW g/plant | CBD yield g/plant |
|---|---|---|---|---|
| Cont. Ex. 1 | 445 | 5.08 | 62.35 | 3.17 |
| Exptl. Ex. 1 | 505 | 5.29 | 73.65 | 3.89 |
| Exptl. Ex. 2 | 515 | 5.63 | 80.76 | 4.55 |
| Exptl. Ex. 3 | 526 | 5.34 | 79.68 | 4.25 |
| Exptl. Ex. 4 | 571 | 5.18 | 72.15 | 3.73 |

The results suggest that the green-yellow light is more effective than the blue light in improving the CBD level. Besides, the green-yellow light with peak wavelength at 515 nm is the most effective one which improves the CBD level up to 10.83%. The green-yellow light is also good for the accumulation of inflorescence weight in cannabis, and improving the CBD yield per plant.

Embodiment 2

Top branches of strong cannabis mother plant are selected as stem cuttings for plant cutting. After the plant cutting is finished (the plant cutting stage is about 2 weeks), the cannabis seedlings with good rooting conditions are transplanted into the rock wool or the substrate for the vegetative growth phase (the vegetative growth stage is about 4 weeks). Each rock wool block has 1 plant, and a density for the transplanted cannabis seedlings is 9 plants/m². The plant is topped when the plant is about 20 cm high for triggering the growth of side branches. After the vegetative growth stage is finished, the plant is moved to the flower promotion stage for flower promotion treatment. The planting density of the plant in the flower promotion stage is 4 plants/m². A distinguishment to the male and female flowers is required. The male flowers are removed, and the female plants is cultivated as before. The cultivation environment is set to have a day and night temperature at 24-26° C./21-22° C., humidity at 60-70%, $CO_2$ concentration at 10000 ppm. Throughout the growth process, the LED light source is used to provide a light environment for the growth of the plant.

An initial light intensity is set to 100 μmol/m²s. As the plant height increases, the light intensity reaches 700 μmol/m²s in the late stage, and the photoperiod is 12 h/d. A light source composed of 20% blue light and 80% red light is provided as the control example 2, wherein the blue light has a peak wavelength at 445 nm, the red light has a peak wavelength at 660 nm. On this basis, light sources having different ratio of green light with peak wavelength at 526 nm added in the control example 2 are provided as experimental examples 5-10 (Table 2). The experimental examples 5-10 also satisfy that a ratio of photon numbers between the red light and the blue light is 4:1. When harvesting, the CBD level in the cannabis is determined, and the dry weight of the inflorescence is collected at the same time to calculate the CBD yield per plant. The experimental results are shown in Table 2.

TABLE 2

| Comb. Irradiation | Ratio of 400-499 nm photons in 380-780 nm light source (%) | Ratio of 600-780 nm photons in 380-780 nm light source (%) | Ratio of 500-599 nm photons in 380-780 nm light source (%) | Peak WL of green light/ nm | CBD level (%) | Inflorescence DW g/plant | CBD yield g/plant |
|---|---|---|---|---|---|---|---|
| Cont. Ex. 2 | 20.0 | 80.0 | 0 | — | 7.41 | 74.52 | 5.52 |
| Exptl. Ex. 5 | 18.4 | 73.6 | 8.0 | 526 | 7.69 | 73.45 | 5.65 |
| Exptl. Ex 6 | 16.8 | 67.2 | 16.0 | 526 | 7.85 | 78.24 | 6.14 |
| Exptl. Ex 7 | 15.0 | 60.0 | 25.0 | 526 | 8.02 | 77.21 | 6.19 |
| Exptl. Ex 8 | 13.2 | 52.8 | 34.0 | 526 | 8.16 | 79.12 | 6.46 |
| Exptl. Ex 9 | 11.6 | 46.4 | 42.0 | 526 | 7.96 | 77.43 | 6.16 |
| Exptl. Ex 10 | 10.0 | 40.0 | 50.0 | 526 | 7.59 | 74.64 | 5.67 |

The results suggest that it is possible to improve the CBD level, up to 10.12%, by adding into the combination of red light and blue light with different ratio of green-yellow light. At the same time, it is beneficial to improve the accumulation of inflorescence weight of cannabis and increase the CBD yield per plant by adding into the combination of red light and blue light with different ratio of green-yellow light.

Embodiment 3

Top branches of strong cannabis mother plant are selected as stem cuttings for plant cutting. After the plant cutting is finished (the plant cutting stage is about 2 weeks), the cannabis seedlings with good rooting conditions are transplanted into the rock wool or the substrate for the vegetative growth phase (the vegetative growth stage is about 4 weeks). Each rock wool block has 1 plant, and a density for the transplanted cannabis seedlings is 9 plants/m². The plant is topped when the plant is about 20 cm high for triggering the growth of side branches. After the vegetative growth stage is finished, the plant is moved to the flower promotion stage for flower promotion treatment. The planting density of the plant in the flower promotion stage is 4 plants/m². A distinguishment to the male and female flowers is required. The male flowers are removed, and the female plants is cultivated as before. The cultivation environment is set to have a day and night temperature at 24-26° C./21-22° C., humidity at 60-70%, $CO_2$ concentration at 10000 ppm. Throughout the growth process, the LED light source is used to provide a light environment for the growth of the plant. An initial light intensity is set to 100 μmol/m²s. As the plant height increases, the light intensity reaches 800 μmol/m²s in the late stage, and the photoperiod is 12 h/d. A light source composed of 20% blue light and 80% red light is provided as the control example 3, wherein the blue light has a peak wavelength at 445 nm, the red light has a peak wavelength at 660 nm. On this basis, same ratio of green lights having different peak wavelengths being added in the control example 3 are provided as experimental examples 11-20 (Table 3). The experimental examples 11-20 also satisfy that a ratio of photon numbers between the red light (600-780 nm) and the blue light (400-499 nm) is 4:1. When harvesting, the CBD level in the cannabis is determined, and the dry weight of the inflorescence is collected at the same time to calculate the CBD yield per plant. The experimental results are shown in Table 3.

TABLE 3

| Comb. Irradiation | Ratio of 400-499 nm photons in 380-780 nm light source (%) | Ratio of 600-780 nm photons in 380-780 nm light source (%) | Ratio of 500-599 nm photons in 380-780 nm light source (%) | Peak WL of green light/ nm | CBD level (%) | Inflorescence DW g/plant | CBD yield g/plant |
|---|---|---|---|---|---|---|---|
| Cont. Ex. 3 | 20 | 80 | 0 | — | 7.52 | 74.70 | 5.62 |
| Exptl. Ex. 11 | 16.4 | 65.6 | 18 | 505 | 8.19 | 75.21 | 6.12 |
| Exptl. Ex 12 | 16.4 | 65.6 | 18 | 511 | 8.28 | 77.84 | 6.38 |
| Exptl. Ex 13 | 16.4 | 65.6 | 18 | 515 | 8.35 | 78.02 | 6.46 |
| Exptl. Ex 14 | 16.4 | 65.6 | 18 | 520 | 8.01 | 79.75 | 6.39 |
| Exptl. Ex 15 | 16.4 | 65.6 | 18 | 523 | 7.98 | 77.65 | 6.20 |
| Exptl. Ex 16 | 16.4 | 65.6 | 18 | 526 | 7.92 | 78.21 | 6.19 |
| Exptl. Ex 17 | 16.4 | 65.6 | 18 | 545 | 7.78 | 77.45 | 6.03 |
| Exptl. Ex 18 | 16.4 | 65.6 | 18 | 565 | 7.74 | 74.06 | 5.73 |
| Exptl. Ex 19 | 16.4 | 65.6 | 18 | 571 | 7.72 | 75.18 | 5.80 |
| Exptl. Ex 20 | 16.4 | 65.6 | 18 | 590 | 8.21 | 77.69 | 6.38 |

The results suggest that, on the basis of adding 18% green-yellow light into the combined red and blue light, green-yellow lights at different wave band in the range of 505-590 nm will results different CBD level. The preferred treatment can promote the CBD level up to 11.04%. At the same time, the green-yellow light is beneficial to improve the accumulation of inflorescence weight of cannabis and increase the CBD yield per plant.

It should be noted that the aforementioned embodiments are merely preferred embodiments of the present disclosure, and those embodiments are not to be deemed as limiting the scope of the invention. The scope of the disclosure should be limited by the by the scope of the claims. It will be apparent to those skilled in the art that other modifications and changes may be made without departing from the spirit and scope of the disclosure.

What is claimed is:

1. A method for promoting accumulation of cannabidiol (CBD) in cannabis, comprising:
    adding an irradiation of a green-yellow light into an indoor growing environment of cannabis to improve the accumulation of level and yield of CBD in cannabis, wherein the green-yellow light has a peak wavelength at 505-590 nm;
    wherein the step of adding the irradiation of green-yellow light having a peak wavelength at 505-590 nm comprises a combined irradiation with other wavelength bands or independent irradiation;
    wherein the combined irradiation or the independent irradiation used in the indoor growing environment of cannabis is a LED light source;
    wherein the LED light source consists of 13.2% blue light, 52.8% red light, and 34.0% green-yellow light;
    wherein in the combined irradiation with other wavelength bands, a ratio of the photon number of the green-yellow light to the photon number of the combined irradiation does not exceed 50%;
    wherein a ratio of a number of the photons of the blue light to a number of the photons of the red light is 1:4;
    wherein an initial light intensity of the combined irradiation or the independent irradiation is 80 $\mu mol/m^2 s$, a maximum light intensity of the combine irradiation or the independent irradiation is 1000 $\mu mol/m^2 s$, and a photoperiod is 10-16 h/d;
    wherein the blue light has a peak wavelength at 445 nm, the red light has a peak wavelength at 660 nm, and the green-yellow light has a peak wavelength at 526 nm.

2. The method of claim 1, wherein the LED light source is realized directly by a LED chip or by using the LED chip to excite a phosphor material.

3. The method of claim 1, wherein the peak wavelength of the green-yellow light lies at 515 nm.

* * * * *